US00PP32351P2

(12) United States Plant Patent
Wood

(10) Patent No.: US PP32,351 P2
(45) Date of Patent: Oct. 20, 2020

(54) ***CORNUS* PLANT NAMED 'SMNCSBD'**

(50) Latin Name: *Cornus stolonifera*
Varietal Denomination: SMNCSBD

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,666

(22) Filed: Nov. 18, 2019

(51) Int. Cl.
*A01H 5/00* (2018.01)
*A01H 6/00* (2018.01)

(52) U.S. Cl.
USPC ..... Plt./220

(58) Field of Classification Search
USPC ..... Plt./216, 220
See application file for complete search history.

*Primary Examiner* — Susan McCormick Ewoldt
(74) *Attorney, Agent, or Firm* — C. A. Whealy

(57) ABSTRACT

A new and distinct cultivar of *Cornus* plant named 'SMNCSBD', characterized by its compact, upright to outwardly spreading and sprawling plant habit; vigorous growth habit; medium green-colored leaves; numerous single-type flowers that are white in color; white to light yellow green-colored fruits; and good garden performance.

3 Drawing Sheets

Botanical classification: *Cornus stolonifera.*
Cultivar designation: 'SMNCSBD'.

BACKGROUND OF THE INVENTION

The present invention relates to a new and distinct cultivar of *Cornus* plant, botanically known as *Cornus stolonifera* and hereinafter referred to by the name 'SMNCSBD'.

The new *Cornus* plant originated from an open-pollination in 2011 of *Cornus stolonifera* 'Flaviramea', not patented, as the female, or seed parent with an unknown selection of *Cornus stolonifera*, as the male, or pollen, parent. The new *Cornus* plant was discovered and selected by the Inventor in 2016 as a single plant within the progeny of the stated open-pollination in a controlled environment in Grand Haven, Mich.

Asexual reproduction of the new *Cornus* plant by softwood stem cuttings in a controlled environment in Grand Haven, Mich. since 2016 has shown that the unique features of this new *Cornus* plant are stable and reproduced true to type in successive generations.

SUMMARY OF THE INVENTION

Plants of the new *Cornus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCSBD'. These characteristics in combination distinguish 'SMNCSBD' as a new and distinct *Cornus* plant:

1. Compact, upright to outwardly spreading and sprawling plant habit.
2. Vigorous growth habit.
3. Medium green-colored leaves.
4. Numerous single-type flowers that are white in color.

5. White to light yellow green-colored fruits.
6. Good garden performance.

Plants of the new *Cornus* differ primarily from plants of the female parent, 'Flaviramea', in growth habit as plants of the new *Cornus* are more compact than plants of 'Flaviramea'.

Plants of the new *Cornus* can be compared to plants of *Cornus baileyii* 'Farrow', disclosed in U.S. Plant Pat. No. 18,523. In side-by-side comparisons, plants of the new *Cornus* differ primarily from plants of 'Farrow' in the following characteristics:

1. Plants of the new *Cornus* are more vigorous than plants of 'Farrow'.
2. Plants of the new *Cornus* have yellow green-colored stems whereas plants of 'Farrow' have red-colored stems.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

Figure 1:
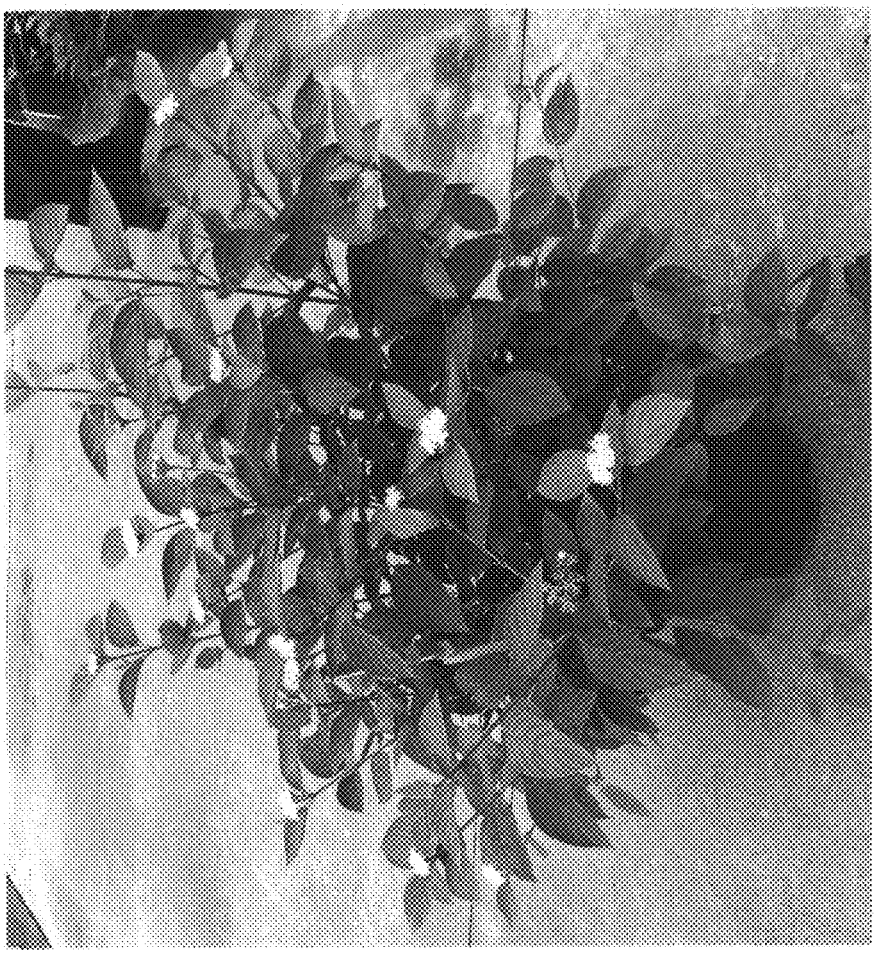

The photograph on the first sheet (FIG. 1 of 3) is a side perspective view of a typical plant grown in a container.

Figure 2:
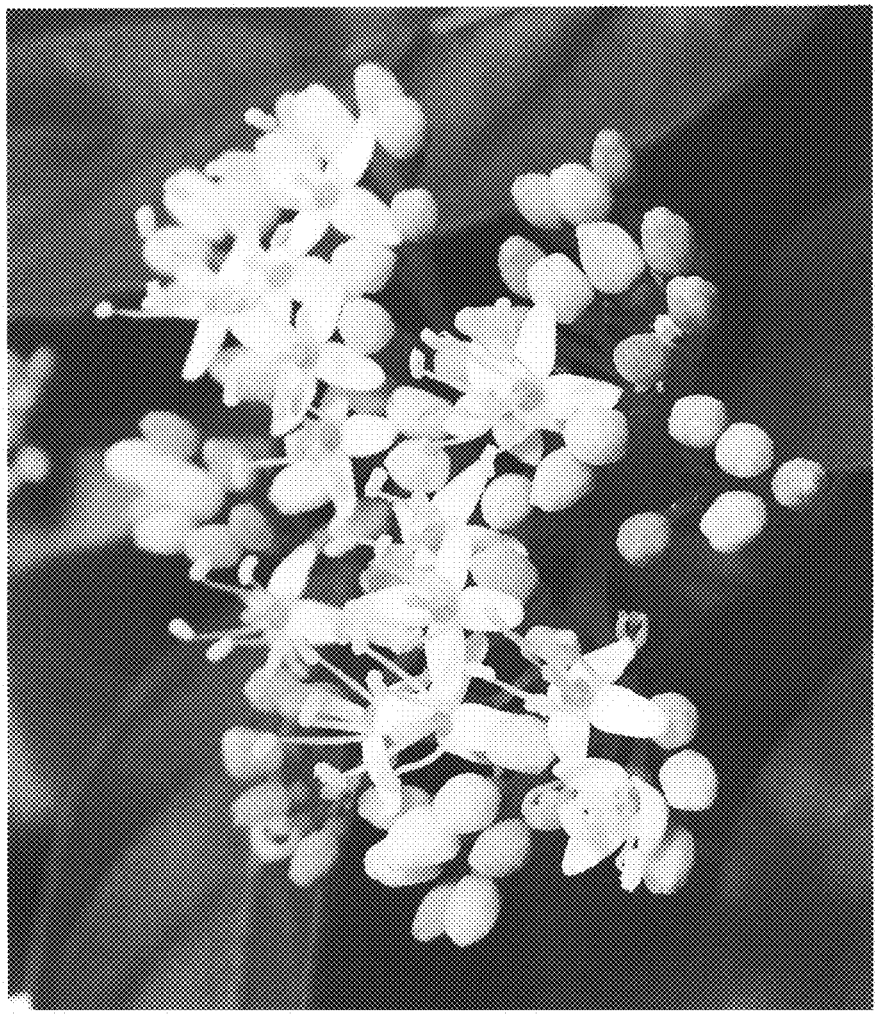
Figure 3:
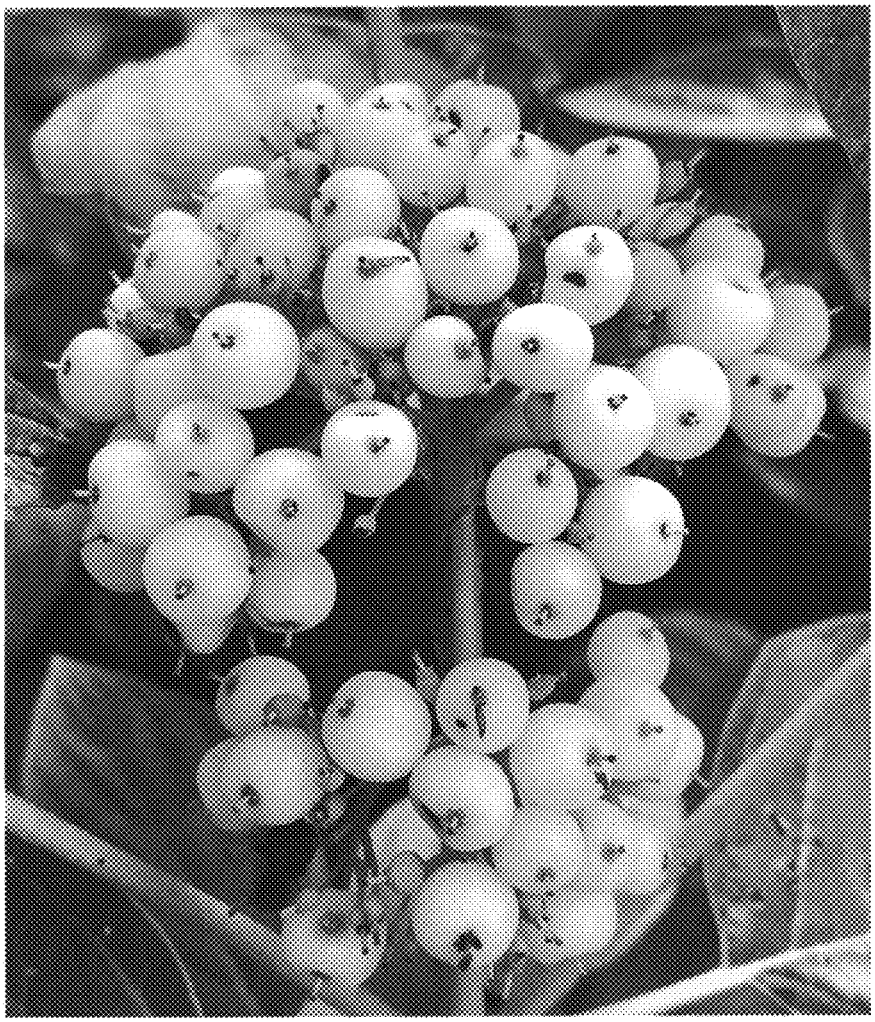

The photograph on the second sheet (FIG. 2 of 3) is a close-up view of typical flowers of a plant of 'SMNCSBD'. The photograph on the third sheet (FIG. 3 of 3) is a close-up view of typical fruits of a plant of 'SMNCSBD'.

DETAILED BOTANICAL DESCRIPTION

Plants used for the aforementioned photographs and the following observations, measurements and values describe plants grown during the summer in five-gallon containers in a polyethylene-covered greenhouse in Grand Haven, Mich.

and under cultural practices typical of commercial *Cornus* production. During the production of the plants, day temperatures ranged from 18° C. to 27° C. and night temperatures ranged from ranged from 5° C. to 10° C. Plants were two years old when the photographs and description was taken. In the following description, color references are made to The Royal Horticultural Society Colour Chart, 2015 Edition, except where general terms of ordinary dictionary significance are used.

Botanical classification: *Cornus stolonifera* 'SMNCSBD'.

Parentage:

*Female, or seed, parent.*—*Cornus stolonifera* 'Flaviramea', not patented.

*Male, or pollen, parent.*—Unknown selection of *Cornus stolonifera*, not patented.

Propagation information:

*Type.*—By softwood stem cuttings.

*Time to initiate roots, summer.*—About one month at temperatures ranging from 18° C. to 27° C.

*Time to produce a rooted young plant, summer.*—About four months at temperatures ranging from 18° C. to 27° C.

*Root description.*—Fine to medium in thickness; typically white to brown in color, actual color of the roots is dependent on substrate composition, water quality, fertilizer, substrate temperature and physiological age of roots.

*Rooting habit.*—Freely branching; dense.

Plant description:

*Plant form and growth habit.*—Upright to outwardly spreading and sprawling perennial shrub; vigorous growth habit; rapid growth rate.

*Plant height.*—About 50 cm.

*Plant width (spread).*—About 86 cm.

*Lateral branches.*—Quantity per plant: Freely branching, about 50. Aspect: Erect to about 15° to 60° from vertical. Length: About 48 cm. Diameter: About 3 mm. Internode length: About 8 cm. Strength: Strong. Texture: Smooth, glabrous. Color: Close to 143B.

Leaf description:

*Arrangement.*—Opposite, simple.

*Length.*—About 10 cm.

*Width.*—About 5 cm.

*Shape.*—Ovate.

*Apex.*—Acute.

*Base.*—Obtuse.

*Margin.*—Entire.

*Texture, upper surface.*—Smooth, glabrous.

*Texture, lower surface.*—Slightly rough, glabrous.

*Venation pattern.*—Pinnate.

*Color.*—Developing and fully developed leaves, upper surface: Close to 137B; venation, close to N144B. Developing and fully developed leaves, lower surface: Close to 148B; venation, close to 145C.

*Petioles.*—Length: About 2 cm. Diameter: About 2 mm. Texture, upper surface: Smooth, glabrous. Texture, lower surface: Pubescent; slightly rough. Color, upper and lower surfaces: Close to 144B.

Flower description:

*Flower appearance and arrangement.*—Upright star-shaped rotate flowers arranged in corymbs with about 50 flowers per inflorescence; flowers face mostly upright.

*Natural flowering season and flower longevity.*—Plants flower during the spring in Michigan; flowers not persistent.

*Fragrance.*—None detected.

*Inflorescence diameter.*—About 5 cm.

*Inflorescence height.*—About 2 cm.

*Flower diameter.*—About 1.2 cm.

*Flower length.*—About 1.2 cm.

*Flower buds.*—Length: About 3 mm. Diameter: About 2 mm. Shape: Ovate to oblong. Color: Close to 145A, becoming closer to 155D with development.

*Petals.*—Quantity and arrangement: Four in a single whorl. Length: About 3 mm. Width: About 2 mm. Shape: Lanceolate. Apex: Acute. Base: Cuneate. Margin: Entire. Texture, upper and lower surfaces: Smooth, glabrous. Color: When opening, upper and lower surfaces: Close to 155D. Fully opened, upper and lower surfaces: Close to 155D.

*Calyx.*—Arrangement and shape: Four sepals fused into a urceolate-shaped calyx. Length: About 2 mm. Diameter: About 2 mm. Texture, upper and lower surfaces: Smooth, glabrous. Color, upper and lower surfaces: Close to N144D.

*Peduncles.*—Length: About 2 cm. Diameter: About 1 mm. Aspect: Upright to about 30° from vertical. Strength: Strong. Texture: Slightly pubescent. Color: Close to 143C.

*Pedicels.*—Length: About 5 mm. Diameter: About 1 mm. Aspect: Upright to about 35° from vertical. Strength: Strong. Texture: Slightly pubescent. Color: Close to 143D.

*Reproductive organs.*—Androecium: Quantity per flower: About four. Filament length: About 3 mm. Filament color: Close to NN155C. Anther length: About 1 mm. Anther shape: Lanceolate, lobed. Anther color: Close to 199C. Pollen amount: None observed. Gynoecium: Quantity per flower: One. Pistil length: About 2 mm. Style length: About 2 mm. Style color: Close to 145C. Stigma shape: Globose. Stigma color: Close to 145C.

*Fruits.*—Quantity: About 100 fruits develop per lateral branch. Length: About 1 cm. Diameter: About 1 cm. Shape: Spherical. Texture: Smooth, glabrous. Color: Close to between NN155B and 145D.

Pathogen & pest resistance: To date, plants of the new *Cornus* have not been observed to be resistant to pathogens and pests common to *Cornus* plants.

Garden performance: Plants of the new *Cornus* have been observed to have good garden performance and to be tolerant to wind, rain, drought, high temperatures about 36° C. and low temperatures about −32° C.

It is claimed:

1. A new and distinct *Cornus* plant named 'SMNCSBD' as illustrated and described.

* * * * *